United States Patent [19]

Finter et al.

[11] Patent Number: 5,153,321

[45] Date of Patent: Oct. 6, 1992

[54] ANTISTATIC AND ELECTRICALLY CONDUCTING POLYMERS AND MOULDING MATERIALS

[75] Inventors: Jürgen Finter, Freibrug, Fed. Rep. of Germany; Bruno Hilti, Basel, Switzerland; Carl W. Mayer, Riehen, Switzerland; Ernst Minder, Basel, Switzerland; Josef Pfeifer, Therwil, Switzerland

[73] Assignee: Ciba-Geigy Corporation, Ardsley, N.Y.

[21] Appl. No.: 718,074

[22] Filed: Jun. 20, 1991

Related U.S. Application Data

[62] Division of Ser. No. 494,061, Mar. 14, 1990, abandoned, which is a division of Ser. No. 172,880, Mar. 25, 1988, Pat. No. 5,009,812.

[30] Foreign Application Priority Data

Apr. 3, 1987 [CH] Switzerland ............... 1284/87

[51] Int. Cl.$^5$ .................................. C07D 345/00
[52] U.S. Cl. ........................ 540/1; 546/256; 549/15; 549/31; 544/338
[58] Field of Search ............... 540/1; 252/500; 546/274, 256; 544/338; 549/83, 31

[56] References Cited

U.S. PATENT DOCUMENTS

| | | | |
|---|---|---|---|
| 3,403,165 | 9/1968 | Matsunaga | 260/327 |
| 3,636,048 | 1/1972 | Klingsberg | 549/31 |
| 4,384,025 | 5/1983 | Hilti et al. | 428/411 |
| 4,522,754 | 6/1985 | Hilti et al. | 428/411 |
| 4,601,853 | 7/1986 | Hilti et al. | 428/411 |
| 4,617,151 | 10/1986 | Mayer et al. | 540/1 |
| 4,801,701 | 1/1989 | Hilti et al. | 540/1 |
| 4,981,962 | 1/1991 | Baumann et al. | 540/1 |
| 5,009,812 | 4/1991 | Finter et al. | 252/500 |

*Primary Examiner*—Karl Group
*Assistant Examiner*—Sue Hollenbeck
*Attorney, Agent, or Firm*—Kevin T. Mansfield; Edward McC. Roberts

[57] ABSTRACT

As a result of the action of electron acceptors, for example chlorine, bromine and/or iodine, on compositions containing a linear, branched or structurally crosslinked polymer and an unsubstituted or substituted tetrathionaphthalene, tetraselenonaphthalene, tetratelluronaphthalene, tetrathiotetracene, tetraselenotetracene or tetratellurotetracene, electrical conductivity is imparted to the compositions through the formation of charge-transfer complexes. These compositions are suitable for the production of mouldings, filaments, fibres, coatings and composite materials which have an antistatic finish or are electrically conducting.

1 Claim, No Drawings

ANTISTATIC AND ELECTRICALLY CONDUCTING POLYMERS AND MOULDING MATERIALS

This is a divisional of Ser. No. 494,061 filed Mar. 14, 1990, abandoned, which is a divisional of Ser. No. 172,880 filed Mar. 25, 1988 now U.S. Pat. No. 5,009,812 issued Apr. 23, 1991.

The invention relates to a plastics composition containing an unsubstituted or substituted tetrathionaphthalene, tetraselenonaphthalene or tetratelluronaphthalene or tetrathiotetracene, tetraseleonotetracene or tetratellurotetracene, to a plastics composition containing a charge-transfer complex (CT complex) formed from these naphthalenes or tetracenes and an electron acceptor, to a process for the preparation of this plastics composition and to the use thereof for the production of mouldings, filaments, fibres, films, coatings and composite materials which have an antistatic finish and/or are electrically conducting.

DE-A 3,005,849 describes electrically conducting moulding materials composed of a thermoplastic and a CT complex, these CT complexes being fibre-shaped or needle-shaped. Compounds containing N, O and/or S are used as the electron donor and polycyano compounds are used as the electron acceptor. The moulding materials can be prepared by adding the acceptor to a polymer solution in which the donor is dissolved and subsequently removing the solvent by evaporation. M. Kryszews ki et al. describe, in Pure and Applied Chemistry, Vol. 56, No. 3, pages 355-368 (1984), electrically conducting polymer compositions containing, as CT complexes, complexes composed of tetrathiotetracene as the electron donor and tetracyanoquinodimethane, tetracyanoethylene or chloranil as the electron acceptor. Because of the relatively low conductivity of the pure CT complexes, the electrical conductivity of these systems is also low.

The stability of the CT complexes containing tetracyanoquinodimethane is low. It is known that these CT complexes have to be stabilized against elimination of HCN, cf. DE-A 3,335,513.

J. C. Stark et al. describe, in Organometallics, 3, pages 732-735 (1984), peri-dichalcogenized polyacenes, certain salts of which possess a high electrical conductivity. Halides of this type are described in U.S. Pat. Nos. 4,384,025, 4,522,754, German Offenlegungsschrift 3,510,072, German Offenlegungsschrift 3,635,124 and EP-A 0,153,905. In general, these halides have a melting point above 300° C. They are also virtually insoluble in organic solvents. Owing to these properties, the halides can only be incorporated into polymers in the form of powders. Polymer compositions of this type have only a very low electrical conductivity, since the conducting particles in the polymer matrix are isolated.

The present invention relates to a composition containing a) a linear, branched or structurally crosslinked polymer which is inert towards component b), and b) a compound of the formula I or Ia or mixtures thereof

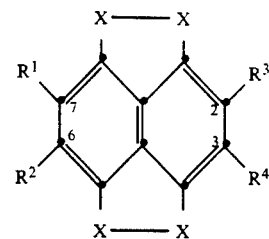

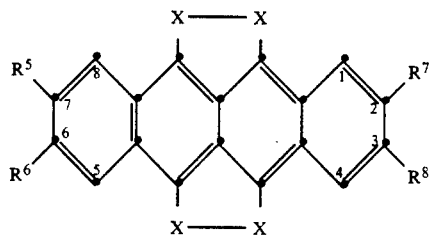

in which X is S, Se or Te, $R^1$, $R^2$, $R^3$ and $R^4$ independently of one another are a hydrogen atom or Cl or $R^1$ and $R^2$ and also $R^3$ and $R^4$ together are each

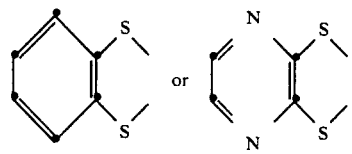

or $R^1$, $R^2$, $R^3$ and $R^4$ are each phenylthio, 4-methylphenylthio, 4-methoxyphenylthio, or 4-pyridylthio, $R^5$, $R^6$, $R^7$ and $R^8$ independently of one another are H or F, $R^5$ is $CH_3$ and $R^6$, $R^7$ and $R^8$ are H, or $R^5$, $R^6$, $R^7$ and $R^8$ are $CH_3$, $R^5$ and $R^6$ are $CH_3$ or Cl, and $R^7$ and $R^8$ are H, or $R^5$ and $R^6$ are H, $R^7$ is $-COR^9$ and $R^8$ is H or $-COR^9$, or $R^5$ and $R^6$ are H and $R^7$ and $R^8$ together are $-CO-O-CO-$ or $-CO-NR^{10}-CO-$ in which $R^9$ is halide, $-OH$, $-NH_2$ or the radical of an alcohol or a primary or secondary amine, or $R^9$ is $-OM$ in which M is a cation, and $R^{10}$ is H or the radical of a primary amine reduced by the $NH_2$ group.

The component b) is preferably present in an amount of 0.01 to 20% by weight, particularly 0.05 to 10% by weight and especially 0.1 to 5% by weight, relative to the polymer.

Some compounds of the component b) and their preparation are described in the publications previously mentioned. Preferred compounds of the component b) are tetrathioteracene, tetraselenotetracene, 2-fluorotetraselenotetracene or 2,3-difluorotetraselenotetracene. Preferred mixtures are those composed of compounds of the formulae I and Ia, the compound of the formula Ia being especially 2,3,6,7-tetrathiophenyltetrathionaphthalene. Mixtures of these tetracenes with a compound of the formula Ia preferably contain 2,3,6,7-tetrathiophenyl-1,4,5,8-tetrathionaphthalene. The novel compounds of the formulae II or IIa

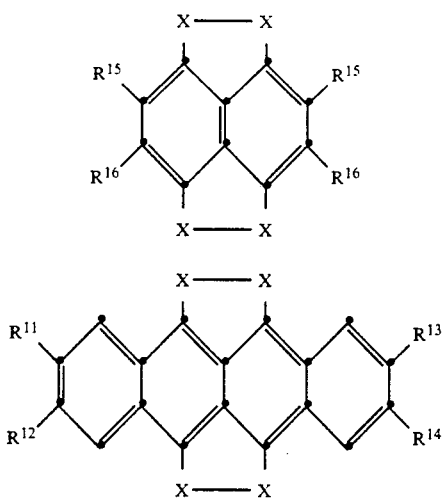

in which $R^{15}$ and $R^{16}$ are each phenylthio, 4-methylphenylthio, 4-methoxyphenylthio or 4-pyridylthio or in which $R^{15}$ and $R^{16}$ together are

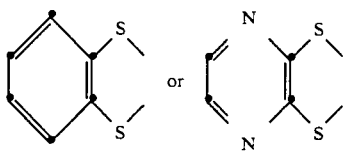

$R^{11}$ is —$CH_3$ and $R^{12}$, $R^{13}$ and $R^{14}$ are H, $R^{11}$ and $R^{12}$ are Cl or $CH_3$ and $R^{13}$ and $R^{14}$ are H, or $R^{11}$, $R^{12}$, $R^{13}$ and $R^{14}$ are —$CH_3$ or F, and X is S, Se or Te, form a further subject of the invention. Their preparation can be carried out as decribed below:

a) Tetramethylated tetracenes

The known starting compounds 4,5-dimethylphthalic anhydride and 2,3-dimethyl-6,7-dihydroxynaphthalene are reacted in the presence of $B_2O_3$ to give 2,3,8,9-tetramethyl-5,12-dihydroxy-6,12-dioxotetracene (A). This reaction and the further chlorination and reduction leading to the product tetrachlorinated in the 5,6,11,12-position are described in German Offenlegungsschrift 3,635,124. The reaction with $Na_2X_2$ leads to the corresponding tetrachalcogenized tetracene. In one variant, 2,3,8,9-tetramethl-5,5,6,11,12,12-hexachlorodihydrotetracene (which is obtained by chlorination with $PCl_5/POCl_3$) is reacted with 1 equivalent of $Na_2Se_2$ and 2 equivalents of $Na_2Se$ to give the corresponding tetraselenotetracene directly. The compound A can also be alkylated with dimethyl sulfate to give the 5,12-dimethoxy derivative [cf. Chem. Pharm. Bull. 20(4), 827 (1972)]. The reaction of this derivative with $P_4S_{10}$ in tetrahydrofuran, subsequent oxidation with $Br_2$ and then reduction with $TiCl_3$ lead to 2,3,8,9-tetramethyl-5,6,11,12-tetrathiotetracene.

c) 2-Methyltetracenes

2-Methyl-5,12-dioxodihydrotetracene is obtained in conformity with the instructions in Chem. Ber. 64, 1713 (1931). The reduction with Zn in alkaline solution gives 2-methyl-5,12-tetrahydrotetracene, which can be dehydrogenated with chloranil to give 2-methyltetracene. The reaction with S (see U.S. Pat. No. 3,723,417) gives 2-methyl-5,6,11,12-tetrathiotetracene. It is also possible to prepare 2-methyl-5,6,11,12-tetrachlorotetracene and to react it with $Na_2X_2$ as described in a).

c) Tetrafluorotetracenes 2,3,8,9-Tetrafluoro-5,12-dihydroxy-6,12-dioxotetracene (B) is obtained in conformity with the instructions in Chem. Ber. 31, 1159 and 1272 (1898) by subjecting 2,3-difluorophthalic anhydride to a condensation reaction with succinic acid and subsequently treating the condensation product with sodium ethylate in ethanol. The further reaction with $PCl_5$, and then with $SnCl_2/CH_3COOH$, to give 2,3,8,9-tetrafluoro-5,6,11,12-tetrachlorotetracene is carried out analogously to the instructions in Zhuv. Org. Kim. 15(2), 391 (1979). Reaction with $Na_2X_2$ gives the corresponding 2,3,8,9-tetrafluorotetrachalcogenotetracenes. Reduction of compound B with Al in cyclohexanol gives 2,3,8,9,-tetrafluorotetracene, which can be reacted with sulfur [see Bull. Soc. Chim. 15, 27 (1948)] to give 2,3,8,9-tetrafluoro-5,6,11,12-tetrathiotetracene.

d) Naphthalenes

The corresponding 2,3,6,7-substituted tetrachalcogenonaphthalenes can be obtained starting from known (see U.S. Pat. No. 3,769,276) 2,3,6,7-tetrachlorotetrachalcogenonaphthalenes by reaction with the potassium salts of thiophenol, 4-methylthiophenol, 4-methoxythiophenol, 4-mercaptopyridine, 1,2-benzodithiol and pyrazine-2,3-dithiol.

e) Dimethyltetracenes and dichlorotetracenes

The procedure is analogous to that described under a), but 4,5-dimethylphthalic anhydride or 4,5-dichlorophthalic anhydride is reacted, as starting compound, with 6,7-dihydroxynaphthalene, and the product is chlorinated with $PCl_5/POCl_3$.

In the formulae I, Ia, II and IIa X is preferably S or Se. $R^9$ as halide is especially chloride.

In the radical —OM, M can be a metal cation or an ammonium cation. Suitable metal cations are, in particular, those of the alkali metals and alkaline earth metals, for example $Li^\oplus$, $Na^\oplus$, $K^\oplus$, $Mg^{2\oplus}$, $Ca^{2\oplus}$, $Sr^{2\oplus}$ and $Ba^{2\oplus}$. $Zn^{2\oplus}$ and $Cd^{2\oplus}$ are also suitable. Examples of suitable ammonium cations are $NH_4^\oplus$ and primary, secondary, tertiary or quaternary ammonium which can preferably contain $C_1$–$C_{12}$alkyl, cyclohexyl, cyclopentyl, phenyl or benzyl groups. The ammonium cations can also be derived from 5-membered or 6-membered heterocyclic amines, for example piperidine, pyrrol and morpholine.

As the radical of an alcohol, $R^9$ is preferably $C_1$–$C_6$alkoxy or $C_2$–$C_6$-hydroxyalkoxy, benzyloxy, phenoxy, cyclopentyloxy or cyclohexyloxy.

As the radical of a primary or secondary amine, $R^9$ is preferably derived from alkylamines having 1 or 2 $C_1$–$C_6$alkyl groups. $R^{10}$ is preferably H, $C_1$–$C_{18}$alkyl, phenyl or benzyl.

As alkyl, $R^{10}$ preferably contains 1 to 12, and particularly 1 to 6, C atoms. The following are examples of alkyl, which can be linear or branched: methyl, ethyl, n-propyl, isopropyl, n-butyl, isobutyl, t-butyl, pentyl, hexyl, 2-ethylhexyl, heptyl, octyl, nonyl, decyl, undecyl and dodecyl. The following are examples of alkoxy and hydroxyalkoxy: methoxy, ethoxy, propoxy, butoxy, pentoxy, hexoxy, β-hydroxyethoxy, γ-hydroxypropoxy, δ-hydroxybutoxy and ω-hydroxyhexoxy.

The polymers of the component a) are inert towards the compounds of the component b). The polymers therefore preferably contain, in the main, no strongly acid groups, for example carboxyl groups, or strongly basic groups, for example primary or secondary amino or hydroxyl groups. The polymers can be, for example, thermosetting plastics, thermoplastics or elastomers.

The following are examples of polymers:

1. Polymers of monoolefins and diolefins, for example polypropylene, polyisobutylene, polybut-1-ene, poly-methylpent-1-ene, polyisoprene or polybutadiene and polymers of cycloolefins, for example cyclopentene or norbornene; and also polyethylene, for example high-density polyethylene (HDPE), low-density polyethylene (LDPE) and low-density, linear polyethylene (LLDPE).

2. Mixtures of the polymers mentioned under 1), for example mixtures of polypropylene with polyisobutylene, polypropylene with polyethylene (for example PP/HDPE or PP/LDPE) and mixtures of different types of polyethylene (for example LDPE/HDPE).

3. Copolymers of monoolefins and diolefins with one another or with other vinyl monomers, for example ethylene/propylene copolymers, propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and terpolymers of ethylene with propylene and a diene, such as hexadiene, dicyclopentadiene or ethylidenenorbornene; and also mixtures of such copolymers with one another and with polymers mentioned under 1), for example polypropylene-ethylene/propylene copolymers, LDPE-ethylene/vinyl acetate copolymers, LDPE-ethylene/acrylic acid ester copolymers, LLDPE-ethylene/vinyl acetate copolymers and LLDPE-ethylene/acrylic acid ester copolymers.

4. Polystyrene, poly-(p-methylstyrene) and poly-(α-methylstyrene).

5. Copolymers of styrene or α-methylstyrene with dienes or acrylic derivatives, for example styrene/-butadiene, styrene/acrylonitrile, styrene/alkyl methacrylate, styrene/butadiene/alkyl acrylate, styrene/-maleic anhydride and styrene/acrylonitrile/methyl acrylate; mixtures of high impact strength obtained from styrene copolymers and another polymer, for example a polyacrylate, a diene polymer or an ethylene/-propylene/diene terpolymer; and also block copolymers of styrene, for example styrene/butadiene/styrene, styrene/isoprene/styrene, styrene/ethylene-butylene/styrene, styrene/ethylene-propylene/styrene or styrene/4-vinylpyridine/styrene.

6. Graft copolymers of styrene or α-methylstyrene, for example styrene on polybutadiene, styrene on polybutadiene/styrene copolymers or polybutadiene/acrylonitrile copolymers, styrene and acrylonitrile (or methacrylonitrile) on polybutadiene; styrene, acrylonitrile and methylmethacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, stryene and acrylonitrile on ethylene/-propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 5), such as are known, for example, as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, especially polymers formed from halogen-containing vinyl compounds, for example polyvinyl chloride, polyvinylidene chloride, polyvinylfluoride or polyvinylidenefluoride; and copolymers thereof, such as vinyl chloride/vinylidene chloride, vinyl chloride/vinyl acetate or vinylidene chloride/vinyl acetate.

8. Polymers derived from derivatives of α, β-unsaturated acids, such as polyacrylates, polymethacrylates and polyacrylonitriles.

9. Copolymers of the monomers mentioned under 8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers, acrylonitrile/alkyl methacrylate/butadiene terpolymers or alkyl methacrylate/4-vinylpyridine copolymers.

10. Polymers derived from acyl derivatives or acetals of unsaturated alcohols, such as polyvinyl acetate, stearate, benzoate or maleate, polyvinyl butyral or polyallyl phthalate; and also copolymers thereof with olefins mentioned in item 1.

11. Homopolymers and copolymers of cyclic ethers, such as polyalkylene glycols, polyethylene oxide, polypropylene oxide or polybutylene glycol.

12. Polyacetals, such as polyoxymethylene and also polyoxymethylenes containing comonomers, for example ethylene oxide; and polyacetals modified with thermoplastic polyurethanes, acrylates or MBS.

13. Polyphenylene oxides and sulfides and mixtures thereof with styrene polymers.

14. Polyurethanes derived on the one hand from polyethers, polyesters and polybutadienes having terminal hydroxyl groups and, on the other hand, from aliphatic or aromatic polyisocyanates, and also precursors thereof.

15. Polyureas, polyimides and polybenzimidazoles. Amongst the polyimides, soluble polyimides are particularly preferred, such as are described, for example, in German Auslegeschrift 1,962,588, EP-A 132,221, EP-A 134,752, EP-A 162,017, EP-A 181,837 and EP-A 182,745.

16. Polycarbonates, polyesters, for example polyalkylene terephthalates, and polyestercarbonates.

17. Polysulfones, polyether-sulfones and polyetherketones.

18. Polyvinylcarbazole.

19. Crosslinkable acrylic resins derived from substituted acrylic acid esters, for example from epoxy-acrylates, urethane-acrylates or polyester-acrylates, for example esters of polyols, such as glycols, trimethylolpropane, pentaerythritol or polyepoxides.

20. Crosslinked epoxide resins derived from polyepoxides, for example from bisglycidyl ethers or from cycloaliphatic diepoxides. They can be crosslinked, for example, by means of anhydrides, by heat using curing accelerators or by the action of UV radiation.

21. Polymer-homologously chemically modified derivatives of cellulose, such as cellulose acetate, propionate and butyrate, and the cellulose ethers, such as methylcellulose.

22. Mixtures (polyblends) of the abovementioned polymers, for example PP/EPDM, PVC/EVA, PVC/ABS, PVC/MBS, PC/ABS, PC/ASA, PC/PBT, PVC/CPE, PVC/acrylate, POM/thermoplastic PUR, PC/thermoplastic PUR, POM/acrylate, POM/M8S and PPO/HIPS.

23. Products which have been crosslinked (vulcanized) with sulfur and are formed from polymers containing double bonds, for example natural rubber, synthetic rubber, butadiene polymers or copolymers or isoprene polymers or copolymers.

A preferred group of thermoplastic polymers is formed by polyolefins, polystyrene, polyvinyl chloride, polyvinylidene chloride, polyvinylidene fluoride, polyacrylates, polymethacrylates, polycarbonates, aromatic polysulfones, aromatic polyethers, aromatic polyethersulfones, polyimides and polyvinylcarbazol.

The composition according to the invention can, in addition, contain a solvent for a soluble polymer and the component b). Examples of suitable solvents are polar, aprotic solvents, which can be used on their own or as mixtures composed of at least two solvents. The following are examples: ethers, such as dibutyl ether, tetrahydrofuran, dioxane, methylene glycol, dimethylethylene glycol, dimethyldiethylene glycol, diethyldiethylene glycol and dimethyltriethylene glycol, halogenated hydrocarbons, such as methylene chloride, chloroform, 1,2-dichloroethane, 1,1,1-trichloroethane and 1,1,2,2-tetrachloroethane, carboxylic acid esters and lactones, such as ethyl acetate, methyl propionate, ethyl benzoate, 2-methoxyethyl acetate, $\gamma$-butyrolactone, $\delta$-valerolactone and pivalolactone, carboxamides and lactams, such as N-methylformamide, N,N-dimethylformamide, N,N-diethylformamide, N,N-dimethylacetamide, N,N-diethylacetamide, $\gamma$-butyrolactam, $\epsilon$-caprolactam, N-methylpyrrolidone, N-acetylpyrrolidone and N-methylcaprolactam, tetramethylurea, hexamethylphosphoric acid triamide, sulfoxides, such as dimethyl sulfoxide, sulfones, such as dimethyl sulfone, diethyl sulfone, trimethylene sulfone and tetramethylene sulfone, N-methylpyrrolidine, N-methylpiperidine, N-methylmorpholine and substituted benzene, such as benzonitrile, chlorobenzene, o-dichlorobenzene, 1,2,4-trichloro-benzene, nitrobenzene, toluene and xylene.

The composition according to the invention can, in addition, contain assistants required for processing and use, for example plasticizers, flow control agents, mould release agents, fillers, fire-retarding agents, antioxidants and light stabilizers, stabilizers, dyes and pigments.

The composition according to the invention can, in addition, contain an electron acceptor, for example an elementary halogen ($Cl_2$, $Br_2$ or $I_2$), or a halogen-containing, organic compound which, if appropriate when energy is supplied, splits off halogen and forms, with a compound of the formula I or Ia (donor), a charge-transfer complex (donor) (halogen)$_x$ in which $0.3 < x < 0.9$. x is preferably $>0.3$ and $<0.8$ and is, in particular, 0.5 for Cl and Br and 0.76 for I. The energy can be, for example, heat energy or radiation energy. In the case of radiation energy, irradiation can be carried out, for example, image-wise through a mask or by the image-wise direction of a beam of light, or area-wise. Heat energy means, for example, a temperature from room temperature to 350° C., in particular 50° to 200° C. The ratio of the electron acceptor to the component b) is preferably 10:1 to 1:5, especially 5:1 to 1:3 and, in particular, 2:1 to 1:2. The electron acceptor, particularly the halogen-containing organic compound, can, however, also be present in appreciably larger amounts and can act at the same time as a solvent for the thermoplastic polymer and the component b), if, for example, the halogen-containing organic compound is a liquid. The organic compound can also be a solid, and it should be miscible and compatible with the polymer.

The organic compound containing halogen, particularly Cl, Br or I, can be a halogenated, saturated or unsaturated, aliphatic, cycloaliphatic, aliphatic-heterocyclic, aromatic or heteroaromatic, organic compound, which can be substituted by —CN, HO—, =O, $C_1$-$C_4$alkyl, $C_1$-$C_4$alkoxy, —CO—$C_1$-$C_4$alkyl or —COOC$_1$-$C_4$alkyl. The halogen compounds can be employed individually or as mixtures. The organic compound is preferably chlorinated and/or brominated. The compounds can be monohalogenated, for example N-brominated or N-chlorinated dicarboximides. C-halogenated compounds advantageously have a higher degree of halogenation; these compounds are preferably C-halogenated, especially C-brominated and/or C-chlorinated, to the extent of at least 80%. Compounds in which the halogen atoms are activated by electron-attracting groups are particularly advantageous. Examples of halogenated organic compounds are tetrabromomethane, bromoform, trichlorobromomethane, hexachloropropene, hexachlorocyclopropane, hexachlorocyclopentadiene, hexachloroethane, N-chlorosuccinimide, octachloropropane, n-octachlorobutane, n-decachlorobutane, tetrabromoethane, hexabromoethane, tetrabromo-o-benzoquinone, 2,4,4,6-tetrabromo-2,5-cyclohexadienone, hexabromobenzene, chloranil, hexachloroacetone, 1,4,5,6,7,7-hexachloro-5-norbornene-2,3-dicarboxylic acid, 1,2,5,6,9,10-hexabromocyclododecane, tetrachloroethylene, perchlorocyclopentadiene, perchlorobutadiene, dichloroacetaldehyde diethyl acetal, 1,4-dichloro-2-butene, 1,3-dichloro-2-butene, 3,4-dichloro-1-butene, tetrachlorocyclopropene, 1,3-dichloroacetone, 2,3,5,6-hexachloro-p-xylene, 1,4-bis-(trichloromethyl)-benzene, 1,3-dibromopropane, 1,6-dibromohexane, ethyl 3-chloropropionate, 3-chlorotoluene, methyl 2-chloropropionate, 2-chloroacrylonitrile, ethyl trichloroacetate, 1,2,3-trichloropropane, 1,1,2-trichloroethane, butyl chloroformate, trichloroethylene, 2,3-dichloromaleic anhydride, 1,12-dibromododecane, $\alpha,\alpha'$-dibromo-p-xylene, $\alpha,\alpha'$-dichloro-o-xylene, phenacyl chloride or bromide, 1,10-dibromodecane, $\alpha,\alpha'$-dichloro-p-xylene, $\alpha,\alpha'$-dibromo-m-xylene, iodoacetonitrile, 2,3-dichloro-5,6-dicyanobenzoquinone, methyl 2,3-dichloropropionate, 1-bromo-2-chloroethane, 1-bromo-2-chloropropane, 2-bromoethyl chloroformate, ethyl iodoacetate, N-chlorosuccinimide, N-bromosuccinimide, N-iodosuccinimide, N-chlorophthalimide, N-bromo-phthalimide or N-iodo-phthalimide or mixtures thereof.

Further examples of suitable electron acceptors are $O_2$ or salts of cations having an oxidative action with non-nucleophilic anions, for example halogen ($F^\ominus$ or $Cl^\ominus$), $BF_4^\ominus$, $SbF_6^\ominus$, $AsF_6^\ominus$ and $PF_6^\ominus$. Examples of cations are the cations of transition metals or rare earth metals [Fe(III), Co(III) or Ce(IV)] or cations of non-metals, for example $NO^+$. $NOBF_4$, $FeCl_3$ or $Co(PF_6)_3$ are examples.

The preparation of the composition according to the invention is effected merely by mixing the components, if appropriate with the concomitant use of a solvent. Shaping can also be combined with mixing, using known methods, for example casting, injection moulding, calendering or extrusion. In the case of thermosetting resins, the compound of the formula I or Ia is advantageously added to a curable component (for example the resin or curing agent), and the curing to give the thermo-setting polymer is carried out after the components have been mixed.

Compositions containing a charge-transfer complex (CT complex) can be prepared in a simple manner from the compositions according to the invention. The invention also relates to a composition containing a) a linear, branched or structurally crosslinked polymer and b) at least one CT complex which is composed of at least one compound of the formulae I or Ia and an electron acceptor. The CT complex can be present, for example, in an amount of 0.01 to 20, preferably 0.1 to 10 and especially 0.1 to 5, % by weight, relative to the polymer.

The CT complexes are preferably chlorides, bromides or iodides of compounds of the formulae I or Ia. The preferences for the compositions described previously apply, moreover.

The preparation of the composition containing CT complexes comprises allowing an electron acceptor to act on a composition according to the invention containing a) a linear, branched or structurally crosslinked polymer and b) at least one compound of the formulae I or Ia.

The electron acceptor is preferably $O_2$, a halogenating agent in the form of gas or vapour, an organic, halogen-containing compound which forms halogen when energy is supplied, especially Cl, Br and/or I, or a salt of a cation having an oxidative action with non-nucleophilic anions.

The action of the electron acceptor is advantageously carried out at temperatures of, for example, room temperature to 350° C., preferably 50° to 200° C.

In one embodiment according to the invention, an electron acceptor in the form of gas or vapour, for example $O_2$, or a halogenating agent, for example $XeF_2$, $Cl^2$, $Br_2$ or $I_2$, is allowed to act on the composition.

A preferred embodiment of the process is one wherein the electron acceptor is a halogen-containing organic compound which is incorporated in the composition and which forms a halide, for example Cl, Br and/or I, when energy is supplied, for example when heated. Heating can mean a temperature up to 350° C., preferably 50°–200° C.

In another embodiment, the composition is mixed with a salt of a cation having an oxidative action with non-nucleophilic anions, and energy, for example heat, is supplied to this mixture.

The organic, halogen-containing compound or a salt can be added at the same time as, or after, the mixing of a polymer with a compound of the formula I and/or Ia. Shaping, for example by casting, injection moulding, extrusion and calendering, can be combined simultaneously with the mixing. When thermosetting polymers are prepared, it is advantageous to incorporate the organic, halogen-containing compound or a salt into a component, for example the epoxide resin in the case of epoxide resins, before the curing or polymerization. The curing or polymerization can then be carried out after the desired shaping.

The temperature required for the liberation of halide, for example Cl, Br and/or I, and for the formation of CT complexes can be achieved by means of curing or polymerization while shaping is carried out and in the case of thermosetting plastics. Heating can, however, also be carried out after shaping. If solvents are concomitantly used, it is advantageous for the heating to remove the solvent.

The compositions according to the invention containing a CT complex are valuable moulding materials from which it is possible to prepare, by customary processes, consumer articles, for example mouldings, sheeting, films, filaments, fibres or coatings, which have an antistatic finish or are electrically conducting.

The invention also relates to the use of the composition described, containing a CT complex, for the production of mouldings, sheeting, filaments, fibres, coatings or composite materials which a) have an antistatic finish and/or b) are electrically conducting.

A preferred field of use is the production of coatings or sheeting by, for example, extrusion or by coating or spreading processes. They can be used for the electrostatic screening of structural components. The sheeting is a flexible electrical conductor from which it is possible to produce electrodes, for example for display elements. Depending on the polymer used, transparent embodiments are also possible.

The compositions according to the invention, containing a CT complex, are distinguished by a high stability to chemicals and resistance to heat and a low migration of the CT complexes. Surprisingly high conductivities have also been achieved, which can amount to up to 25% of the conductivity of the pure CT complexes. The CT complexes form a network of electrically conducting crystal needles in the polymer matrix.

The following examples illustrate the inventions in greater detail.

A) The Preparation of Starting Materials a1) The preparation of 2,3,8,9-tetramethyl-5,6,11,12-tetrathiotetracene 0.6 g (1.6 mmol) of 2,3,8,9-tetramethyl-5,11-dimethoxytetracene-6,12-quinone, 0.75 g (1.68 mmol) of $P_4S_{10}$, 0.1 g of sulfur and 50 ml of dioxane are mixed and are heated under reflux for 22 hours. The precipitate is filtered off while hot, washed with dioxane and then with chloroform and dried in a high vacuum. This gives 0.6 g of product, which is stirred for 5 minutes in 100 ml of formic acid in an ultrasonic bath. 10 ml of 1% $Br_2$ solution are added dropwise, the mixture is heated under reflux and a further 7 ml of $Br_2$ solution are added dropwise. The insoluble constituents are filtered off. The solution is diluted with 500 ml of water and reduced by means of acid $TiCl_3$ solution (Merck, approx. 15% of $TiCl^3$ in 10% hydrochloric acid). The resulting precipitate is filtered off with suction under an argon atmosphere, washed with water and dried in a high vacuum. This gives 0.4 g (61% of theory) of crude product, which is sublimed at 270° C./0.13 pascal. 70 mg of 2,3,8,9-tetramethyl-5,6,11,12-tetrathiotetracene are obtained in the form of black crystals. Mass spectrum:

$M^+ = 408$.

$\nu_{max}$ (1,2,4-trichlorobenzene): 691 nm.

a2) Preparation of 2,3,8,9-tetramethyl-5,6,11,12-tetraselenotetracene

1) Chlorination of 2,3,8,9-tetramethyl-6,11-dihydroxytetracene-5,12-quinone 40.99 g of phosphorus pentachloride are dissolved in 102.5 ml of phosphoryl chloride at 75° C. under a gentle stream of argon in a 350 ml sulfonation flask equipped with a gas inlet tube, a thermometer and a reflux condenser. 12.2 g (0.035 mol) of 2,3,8,9-tetramethyl-6,11-dihydroxytetracene-5,12-quinone are then added to this clear, yellowish solution; the red suspension is heated under reflux for 4 hours. In the course of this, a suspension of a beige colour is gradually formed. After being cooled to room temperature, the reaction mixture is filtered and the beige solid is thoroughly washed with acetic acid and dried at 50° C. ($1.3 \times 10^{-2}$ mbar). This gives 12.4 g (71% yield) of 2,3,8,9-tetramethyl-5,5,6,11,12,12-hexachlorotetracene. Mass spectrum: $M^+ = 490$ (6Cl).

2) Preparation of 2,3,8,9-tetramethyl-5,6,11,12-tetraselenotetracene 1.58 g (20 milliequivalents) of selenium (Ventron, 99.9999%) and 0.69 g of Na (30 milliequivalents) are reacted in 150 ml of dimethylformamide (DMF) (dried through an A4 molecular sieve) at 130° C. and under a gentle stream of argon in a 250 ml three-necked flask equipped with a gas inlet tube and a reflux condenser to give a mixture of $Na_2Se$ (20 mmol) and $Na_2Se_2$ (10 mmol). 2.47 g (5 mmol) of 2,3,8,9-tetramethyl-5,5,6,11,12,12-hexachlorotetracene are then added at the same temperature. The colour of the reaction mixture immediately changes to deep green. After a reaction time of 20 hours, the mixture is cooled to room temperature and the black solid with a blue-green irridescence is filtered off with suction, washed with DMF, water and acetone (3 50 ml portions of each) and dried at 50° C. ($1.3 \times 10^{-2}$ mbar). Crude yield 2.06 g (69%). This crude product is suspended in 200 ml of anhydrous formic acid and is oxidized by passing in oxygen. The blue solution of the cation radical is filtered and Ti-III chloride solution (15% of $TiCl_3$ in 10% hydrochloric acid) is added until the solution has a permanent slight red-violet colour. In the course of this, 2,3,8,9-tetramethyl-5,6,11,12-tetraselenotetracene is deposited in the form of a flocculant, vividly green precipitate. It is filtered off and the solid is washed with water until the eluate is colourless and neutral. After being dried at 50° C. ($1.3 \times 10^{-2}$ mbar) the product is sublimed at approx. 300° C. and $1.3 \times 10^{-3}$ mbar. Small black needles are formed. $\lambda_{max}$ (1,2,4-trichlorobenzene): 693, 639 and 462 nm. Mass spectrum: $M^+ = 596$ (4Se). The fragmentation is in agreement with the expected structure.

b) Preparation of 2-methyl-5,6,11,12-tetrathiotetracene 1.7 g (7 mmol) of 2-methyltetracene and 3.4 g (100 mmol) of sulfur in 40 ml of freshly distilled dimethylformamide, dried through a molecular sieve, are kept under reflux for 4 hours. After cooling, the black-green precipitate is filtered off. 2 g (78% of theory) of crude product are obtained, and are recrystallized from 200 ml of chlorobenzene.

1.2 g of 2-methyl-5,6,11,12-tetrathiotetracene are obtained in the form of black crystalline needles. Mass spectrum: $M^+ = 366$. $\lambda_{max}$ (1,2,4-trichlorobenzene): 705 nm.

c) Preparation of 2,3,8,9-tetrafluoro-5,6,11,12-tetrathiotetracene 30 mg (0.1 mmol) of 2,3,8,9-tetrafluorotetracene and 22 mg of sulfur (0.68 milliequivalent) in 5 ml of 1,2,4-trichlorobenzene are heated under reflux for 72 hours under argon. When the reaction solution has cooled, the precipitated 2,3,8,9-tetrafluoro-5,6,11,12-tetrathiotetracene is filtered off and washed with trichlorobenzene and acetone until the filtrate is colourless. 25 mg of a black-green powder are obtained (58.9% of theory).

$\lambda_{max}$ (1,2,4-trichlorobenzene): 702 nm. Mass spectrum: $M^+ = 424$.

d) Preparation of 2,3,8,9-tetrafluoro-5,6,11,12-tetraselenotetracene 37 mg (1.6 mmol) of Na and 125 mg (1.55 mmol) of Se are reacted in 10 ml of dimethylformamide (DMF, twice distilled and dried through a molecular sieve) at an internal temperature of 110° C., under argon and with stirring, in a 50 ml flask to give $Na_2Se_2$. The reaction time is 1 hour. A red solution with a little red-brown precipitate is formed. 162 mg (0.58 mmol) of 2,3,8,9-tetrafluoro-5,6,11,12-tetrachlorotetracene, suspended in 10 ml of DMF, are then added to the $Na_2Se_2$ solution, which has been cooled to 55° C. The mixture is kept at this temperature for 20 hours. The precipitate is then filtered off with suction, washed with DMF, $CHCl_3$, benzene and acetone (3 portions of approx. 10 ml of each) and dried in a high vacuum at 50° C. 263 mg of crude product are obtained (>100% of theory; still contains NaCl). The crude product is suspended in 50 ml of formic acid and oxidized with oxygen. This gives a blue solution, which is filtered. The solution is then diluted with three times its volume of water and reduced with $TiCl_3$ solution (Merck: approx. 15% of $TiCl_3$ in 10% hydrochloric acid) until the red-violet colour of the reducing agent is retained. The product is precipitated in the form of a green, flocculant precipitate. It is filtered off with suction, washed with water and dried in a high vacuum at 50° C. 160 mg of pre-purified product are obtained (68% of theory).

The pre-purified product is sublimed at 270° C./0.13 pascal. This gives 51.5 mg of black-green needles. Mass spectrum: $M^+ = 616$ (cluster having 4 Se). $\lambda_{max}$: 712 nm.

e) Preparation of 2,3-dichloro-5,6,11,12-tetraselenotetracene 408 mg (2 mmol) of $Na_2Se_2$ in 40 ml of DMF are prepared analogously to Example d), and 432 mg (1 mmol) of 2,3,5,6,11,12-hexachlorotetracene in 30 ml of DMF are added. The temperature is kept at 80° C. for 24 hours. The black precipitate is then filtered off with suction and washed with DMF, $CHCl_3$, benzene, acetone and water (3 20 ml portions of each). This gives 600 mg of crude product, which, after being dried, is sublimed at 290° C. ($1.3 \times 10_{-2}$ mbar); this gives 214 mg (35.2%) of small black needles of 2,3-dichloro-5,6,11,12-tetraselenotetracene. $\lambda_{max}$ in trichlorobenzene: 746, 690 and 540 nm. Mass spectrum: $M^+ = 608$ (4Se, 2Cl). The fragmentation is in agreement with the structure.

f) Preparation of 2-fluoro-5,6,11,12-tetratellurotetracene 205 g (16 mmol) of tellurium and 368 mg (16 mmol) of sodium in 30 ml of DMF (dried through an A4 molecular sieve) are reacted at 110° C. for 1¼ hours under a gentle stream of argon in a 200 ml sulfonation flask equipped with a reflux condenser and a gas inlet tube and also a thermometer, to give $Na_2Te_2$ (8 mmol). The solution is cooled to 50° C. and a suspension of 1.4 g (3.66 mmol) of 2-fluoro-5,6,11,12-tetrachlorotetracene in 30 ml of dry DMF is added to it, and the mixture is stirred at 50° C. for 92 hours. The green solution is filtered under argon, and the grey-black precipitate is washed with DMF, benzene and acetone (3 25 ml portions of each). The crude product, 3.23 g (>100%; still contains sodium chloride), is recrystallized from 6 l of chlorobenzene under an atmosphere of argon and in a brown-coloured flask. This gives 660 mg (24%) of pure 2-fluoro-5,6,11,12-tetra-tellurotetracene in the form of small black needles having a silvery lustre. UV-vis spectrum: $\lambda_{max}$ (1,2,4-trichlorobenzene) = 766, 708 (shoulder) and 464 nm. Mass spectrum: M+ = 754 (4Te). The fragmentation is in agreement with the expected structure.

g) Preparation of

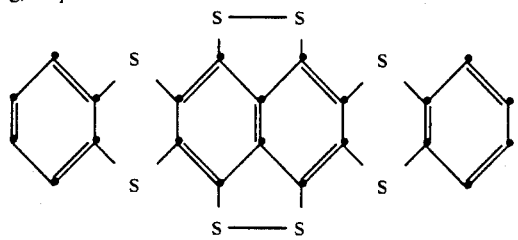

1.0 g (1.04 mmol) of 1,2-benzenedithiol, 0.78 g (13.93 mmol) of KOH and 300 ml of dimethylacetamide (DMA) are mixed under an atmosphere of argon and heated to reflux temperature. DMA is then distilled off until the boiling point has risen to approx. 165° C. (approx. 100 ml). The mixture is allowed to cool somewhat, 1.36 g (3.5 mmol) of 2,3,6,7-tetrachloro-1,4,5,8-tetrathionaphthalene are added and the mixture is heated under reflux for 30 minutes. It is then diluted with 400 ml of water, and the precipitate is filtered off with suction, washed with water, ethanol and chloroform and dried in a high vacuum. 1.55 g of crude product (84% of theory) are obtained. Sublimation at 360° C./0.13 pascal gives 1.126 g of brown needles. Mass spectrum: M+ = 528. $\lambda_{max}$ (1,2,4-trichlorobenzene): 445 nm.

| Elementary analysis: | % C | % H | % S |
| --- | --- | --- | --- |
| Calculated: | 49.97 | 1.53 | 48.5 |
| Found: | 50.09 | 1.45 | 48.8 | h) Preparation of

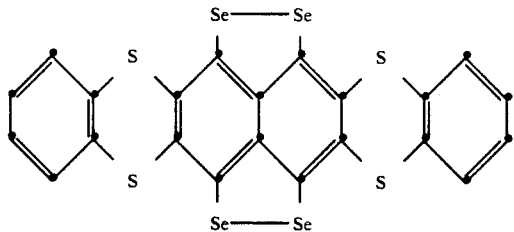

535 mg (3.76 mmol) of 1,2-benzenedithiol, 422 mg (7.53 mmol) of KOH and 200 ml of DMA are mixed under an atmosphere of argon and are heated to reflux temperature. 50 ml of DMA are distilled off, the residue is cooled slightly and 534 mg (0.92 mmol) of 2,3,6,7-tetrachloro-1,4,5,8-tetraselenonaphthalene are added. The mixture is kept under reflux for 45 minutes. After it has cooled, the precipitate is filtered off with suction. The precipitate is washed with DMA water, ethanol and chloroform and dried in a high vacuum. This gives 288 mg (43% of theory) of crude product. 100 mg of the crude product are sublimed at 360° C./0.13 pascal. 85 mg of rust-brown needles are obtained. Mass spectrum: M+ = 720 (cluster of 4Se). $\lambda_{max}$ (1,2,4-trichlorobenzene): 460 nm.

i) Preparation of

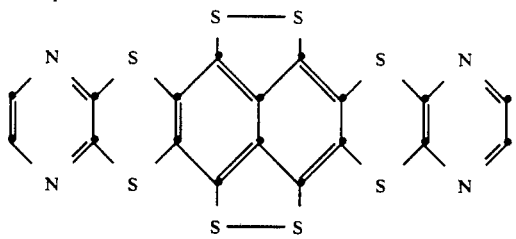

144 mg (1 mmol) of pyrazine-2,3-dithiol, 1.12 mg (2 mmol) of KOH and 45 ml of DMA are mixed under an atmosphere of argon and are heated to reflux temperature. The mixture is kept under reflux for 30 minutes and 15 ml of DMA are then distilled off. The mixture is allowed to cool slightly, 194 mg (0.5 mmol) of 2,3,6,7-tetrachloro-1,4,5,8-tetrathionaphthalene are added, and the mixture is heated under reflux for 30 minutes. After it has cooled, the precipitate is filtered off, washed with DMA, water and ethanol and dried in a high vacuum. This gives 14 mg (5% of theory) of crude product. Sublimation at 360° C./0.13 pascal gives rust-brown crystals. Mass spectrum: M+ = 532. $\lambda_{max}$ (1,2,4-trichlorobenzene): 435 nm.

j) Preparation of 2,3,6,7-(tetraphenylthio)-1,4,5,8-tetranaphthalene 220 mg (2 mmol) of thiophenol, 112 mg of KOH and 50 ml of DMA are mixed under an atmosphere of argon and are heated to reflux temperature. 15 ml of DMA are distilled off. The mixture is allowed to cool slightly, 194 mg (0.5 mmol) of 2,3,6,7-tetrachloro-1,4,5,8-tetrathionaphthalene are added and the mixture is kept under reflux for one hour. After it has cooled, the brown-red precipitate is filtered off with suction, washed with DMA, water, ethanol and chloroform and dried in a high vacuum. This gives 212 mg (61.9% of theory) of crude product. Sublimation at 265° C./0.13 pascal gives scarlet-red, transparent crystal rodlets. Melting point: 285° C.

Mass spectrum: M+ = 684. $\lambda_{max}$ (1,2,4-trichlorobenzene): 516 nm.

k) Preparation of 2,3,6,7-(tetramethoxyphenyl)-tetrathiotetracene (A) and 2,3,6,7-tetra-(4-pyridylthio)-tetracene (B)

The compounds A and B are obtained if 4-methoxythiophenol and 4-mercaptopyridine, respectively, are used instead of thiophenol under conditions otherwise identical to those in Preparation Example j).

| | UV-vis spectrum $\lambda_{max}$ (nm) (1,2,4-trichlorobenzene) | Mass spectrum [M+] | Sublimation temperature (°C.) |
| --- | --- | --- | --- |
| A | 508 | 804 | ~240 [melts before |
| B | 526 | 688 | ~300 sublimation] | l) Preparation of 2,3,6,7-(tetraphenylthio)-1,4,5,8-tetraselenonaphthalene 2,3,6,7-Tetrachloro-1,4,5,8-tetraselenonaphthalene is reacted, instead of 2,3,6,7-tetrachloro-1,4,5,8-tetrathionaphthalene, with thiophenolate under conditions identical with those in Preparation Example j). Yield: 33.2%. Sublimation at 310° C. ($1.3 \times 10^{-3}$ mbar) gives brick-red platelets. $\lambda_{max}$ (1,2,4-trichlorobenzene): 530 (shoulder), 469 nm; mass spectrum: M+: 872 (4Se). The fragmentation is in agreement with the expected structure.

USE EXAMPLES

EXAMPLES 1-4

Preparation of electrically conducting polymer films by means of a gaseous electron acceptor A tetraselenotetracene and a polymer are dissolved in a solvent with heating. The solution is poured onto a heated sheet of glass, and the solvent is removed by evaporation. The film is treated, at the temperature of evaporation, with a gaseous electron acceptor. The treatment is terminated before the film has a pronounced red coloration. This point in time is determined previously by trials. Further data can be seen in Table 1, where the volume resistivity is also given.

TABLE 1

| Example No. | Polymer (1) | mg of TSeT (2) | 9.9 g of solvent | Electron acceptor | Evaporation temperature [°C.] | Volume resistivity [Ohm × cm] |
|---|---|---|---|---|---|---|
| 1 | PVC (Vinnol H70 DF/Wacker) | 1.6 of 2-FTSet | Nitrobenzene | Chlorine | 150 | 50 |
| 2 | Polyimide (3) | 2 of TSeT | 1,2-Dichlorobenzene | Chlorine | 140 | 14 |
| 3 | Polyimide (4) | 2 of TSeT | 1,2-Dichlorobenzene | Atmospheric oxygen | 120 | $7.8 \times 10^2$ |
| 4 | PVC (Vinnol H70 DF/Wacker) | 1.6 of 2,3,8,9-$F_4$TSet | Nitrobenzene | Chlorine | 150 | $4.1 \times 10^5$ |

(1) 100 mg
(2) Tetraselenotetracene
(3) formed from pyromellitic dianhydride and 2-methyl-4,6-diethyl-1,5-diaminobenzene. $\eta$ = 0.5 dl/g (25° C., N-methylpyrrolidone)
(4) formed from pyromellitic dianhydride, 2-methyl-4,6-diethyl-1,5-diaminobenzene (60 mol %, relative to diamines) and 2,2'-dimethyl-4,4'-diaminodiphenylmethane (40 mol %), $\eta$ = 0.92 dl/g (25° C., N-methyl-pyrrolidone)

EXAMPLES 5-25

Preparation of electrically conducting polymer films using a liquid or solid halogen-forming compound 100 mg of polymer (200 mg in Example 10) and a tetraselenotetracene are dissolved in a solvent I. A halogen-forming compound which, in turn, is dissolved in a solvent II is then added to the solution (Examples 5, 8, 9, 12, 13, 18–22 and 25). The solution is poured onto a heated sheet of glass, and the solvent is removed by evaporation at an elevated temperature. The volume resistivity is then determined. Further data can be seen in Table 2.

TABLE 2

| Example No. | Polymer | Amount of TSet (2) [mg] | Solvent I [Amount in g] | Halogen-forming compound | Solvent II [Amount in ml] | Evaporation temperature °C. | Volume resistivity [Ohm × cm] |
|---|---|---|---|---|---|---|---|
| 5 | Polysulfone (5) Resin (Polyscience) | 2,3-$F_2$TSeT [1.6] | Nitrobenzene [6.3] | Tetrabromomethane [6.0 mg] | Nitrobenzene [3.0] | 130 | 0.97 |
| 6 | PVC (Vinnol H70 DF, Wacker) | 2-FTSeT [1.6] | 1,2-Dichlorobenzene [8.9] | Bromoform [$5.8 \times 10^3$ mg] | — | 130 | 12.6 |
| 7 | Polysulfone (6) (Victrex 4800 P) | TSeT [1.6] | Nitrobenzene [7.5] | Bromoform [$5.8 \times 10^3$ mg] | — | 120 | 0.2 |
| 8 | Polysulfone (6) (Victrex 4800 P) | 2-FTSeT [1.7] | Nitrobenzene [7.5] | o-Chloranil [0.7 mg] | 1,2-Dichlorobenzene [1.0] | 130 | 122 |
| 9 | Polysulfone (5) Resin | 2-FTSeT [1.6] | Dimethylformamide [6.0] | Hexachloropropane [4.2 mg] | Dimethylformamid [2.0] | 120 | 0.56 |
| 10 | Polyimide (3) | 2-FTSeT [1.6] | Nitrobenzene [4.0] | Bromoform [$5.8 \times 10^3$ mg] | — | 130 | 9.0 |
| 11 | Polyimide (4) | TSeT [1.6] | Nitrobenzene [9.9] | Bromoform [$5.8 \times 10^3$ mg] | — | 160 | 0.44 |
| 12 | Polysulfone (5) Resin | TSeT [1.6] | 1,2,4-Trichlorobenzene [7.5] | Hexachloropropene [1.9 mg] | 1,2,4-Trichlorobenzene [2.0] | 160 | 0.17 |
| 13 | Polysulfone (5) Resin | TSeT [1.6] | γ-Butyrolactone [7.5] | Hexachloropropene [1.9 mg] | γ-Butyrolactone [2.0] | 130 | 2.1 |
| 14 | Polyamide (4) | TSeT [1.6] | DMF [9.8] | Perchlorobutadiene [5 μl] | — | 100 | 2.6 |
| 15 | Polyimide (4) | TSeT [1.6] | DMF [9.8] | Dichloroacetaldehyde diethyl acetal [5 μl] | — | 90 | 7.6 |
| 16 | Polyimide (4) | TSeT [1.6] | DMF [9.8] | 1,4-Dichloro-2-butene [5 μl] | — | 120 | 2.7 |
| 17 | Polyimide (4) | TSeT [1.6] | DMF [9.8] | 1,3-Dichloro-2-butene [5 μl] | — | 110 | 0.48 |
| 18 | Polyimide (4) | TSeT [1.6] | DMF [9.8] | 1,3-Dichloroacetone [5 mg] | DMF [2.0] | 130 | 13.7 |
| 19 | Polyimide (4) | TSeT [1.6] | DMF [9.8] | α,α',2,3,5,6-Hexachloro-p-xylene [5 mg] | DMF [2.0] | 90 | 0.80 |
| 20 | Polyimide (4) | TSeT [1.6] | DMF [9.8] | 1,4-Bis(trichloromethyl)-benzene [5 mg] | DMF [2.0] | 130 | 4.9 |

TABLE 2-continued

| Example No. | Polymer | Amount of TSet (2) [mg] | Solvent I [Amount in g] | Halogen-forming compound | Solvent II [Amount in ml] | Evaporation temperature °C. | Volume resistivity [Ohm × cm] |
|---|---|---|---|---|---|---|---|
| 21 | Polycarbonate (9) | TSeT [1.6] | 1,2,4-Trichloro-benzene [9.0] | Hexachloropropene [5.1 mg] | 1,2,4-Trichloro-benzene [2.0] | 170 | 0.25 |
| 22 | Polycarbonate (9) | TSeT [1.6] | Chlorobenzene [7.0] | Hexachloropropene [5.2 mg] | Chlorobenzene [1.6] | 120 | 472 |
| 23 | Polyimide (3) | TSeT [1.6] | DMF [9.8] | Iodoacetonitrile [5 μl] | — | 130 | 1.2 |
| 24 | Polycarbonate (9) | TTT [1.6] (7) | 1,2-Dichloro-benzene [9.9] | Diiodomethane [0.4 ml] | — | 140 | 30 |
| 25 | Polycarbonate (9) | TPT-TTN [1.6] (8) | Methylene dichloride [10.3] | Bromine [5.56 mg] | Methylene dichloride [1.0] | 30 | $2.9 \cdot 10^5$ |

(2) as Table 1
(3) as Table 1
(4) as Table 1
(5) —(O—C$_6$H$_4$—C(CH$_3$)$_2$—C$_6$H$_4$—O—C$_6$H$_4$—SO$_2$—C$_6$H$_4$)$_n$—
(6) —(C$_6$H$_4$—O—C$_6$H$_4$—SO$_2$)$_n$—
(7) Tetrathiotetracene
(8) 2,3,6,7-Tetraphenylthio-1,4,5,8-tetrathionaphthalene
(9) Bisphenol A polycarbonate (PC 3000 W)

EXAMPLE 26

1.6 mg of TSeT, 1.6 mg of 2,3,6,7-(tetraphenylthio)-1,4,5,8-tetrathionaphthalene and 100 mg of polycarbonate are dissolved in 9.0 g of 1,2,4-trichlorobenzene. 5.1 mg of hexachloropropene in 2.0 ml of 1,2,4-trichlorobenzene are added to the solution. 1.3 ml of the solution are used to cast a film. The solvent is removed by evaporation at 150° C. A film having a volume resistivity of 0.15 Ω cm and pronounced metallic properties is obtained. The addition of 2,3,6,7-(tetraphenyl-thio)-1,4,5,8-tetrathionaphthalene on its own produces films having a substantially higher volume resistivity (see Example 25). Films containing TSeT as the sole additive also exhibit an even higher volume resistivity (see Example 21).

EXAMPLES 27-75

100 mg of polymer and 1.6 mg of tetraselenotetracene are dissolved in a solvent. A solution of a halogen-containing compound is then added to this solution, as an electron acceptor. The solution is poured onto a heated sheet of glass; the solvent is allowed to evaporate under isothermal conditions at temperatures between 100° and 130° C. The compounds tested are shown in Table 3. In all cases conducting polymer films having an electrically conducting network of crystal needles are obtained. The conductivity is between 0.1 and 5 Scm$^{-1}$.

TABLE 3

| Example No. | Polymer | Halogen compound | Solvent |
|---|---|---|---|
| 27 | PI | 1,12-Dibromododecane | DMF |
| 28 | PI | α,α'-Dibromo-p-xylene | DMF |
| 29 | PI | Phenacyl chloride | DMF |
| 30 | PI | α,α'-Dichloro-o-xylene | DMF |
| 31 | PI | Phenacyl bromide | DMF |
| 32 | PI | 1,10-Dibromodecane | DMF |
| 33 | PI | α,α'-Dichloro-p-xylene | DMF |
| 34 | PI | α,α'-Dibromo-m-xylene | DMF |
| 35 | PI | Iodoacetonitrile | DMF |
| 36 | PI | Methyl 2,3-dichloropropionate | DMF |
| 37 | Polyarylate | Hexachloropropene | DMF |
| 38 | PI | 1:1 Hexachloropropene and 1,1,2-trichloroethane | DMF |
| 39 | PI | 1:1 Hexachloropropene and 1,6-dibromohexane | DMF |
| 40 | PI | 1:1 Hexachloropropene and iodoacetonitrile | DMF |

TABLE 3-continued

| Example No. | Polymer | Halogen compound | Solvent |
|---|---|---|---|
| 41 | PI | 1:1 1,6-Dibromohexane and iodoacetonitrile | DMF |
| 42 | PI | Iodoacetonitrile | DMF |
| 43 | PI | 1-Bromo-2-chloroethane | DMF |
| 44 | PI | 1-Bromo-2-chloropropane | DMF |
| 45 | PI | 2-Bromoethyl chloroformate | DMF |
| 46 | PI | Ethyl iodoacetate | DMF |
| 47 | PI | N-Bromosuccinimide | DMF |
| 48 | PI | N-Chlorosuccinimide | DMF |
| 49 | PI | N-Iodosuccinimide | TCB |
| 50 | PC | Hexachloroacetone | TCB |
| 51 | PC | 1,4,5,6,7,7-Hexachloro-5-norbornene-2,3-dicarboxylic anhydride | TCB |
| 52 | PC | 1,2,5,6,9,10-Hexabromo-cyclododecane | DMF |
| 53 | PI | Tetrachloroethylene | DMF |
| 54 | PI | Perchlorocyclopentadiene | DMF |
| 55 | PI | Perchlorobutadiene | DMF |
| 56 | PI | Dichloroacetaldehyde diethyl acetal | DMF |
| 57 | PI | 1,4-Dichloro-2-butene | |
| 58 | PI | 1,3-Dichloro-2-butene | DMF |
| 59 | PI | 3,4-Dichloro-1-butene | DMF |
| 60 | PI | Tetrachlorocyclopropene | DMF |
| 61 | PI | 1,3-Dichloroacetone | DMF |
| 62 | PI | 2,3,5,6-Hexachloro-p-xylene | DMF |
| 63 | PI | 1,4-Bis(trichloromethyl)-benzene | DMF |
| 64 | PI | 1,3-Dibromo-propane | DMF |
| 65 | PI | 1,6-Dibromo-hexane | DMF |
| 66 | PI | Ethyl 3-chloropropionate | DMF |
| 67 | PI | 3-Chloro-toluene | DMF |
| 68 | PI | Methyl 2-chloropropionate | DMF |
| 69 | PI | 2-Chloroacrylonitrile | DMF |
| 70 | PI | Ethyl trichloroacetate | DMF |
| 71 | PI | 1,2,3,-Trichloropropane | DMF |
| 72 | PI | 1,1,2-Trichloroethane | DMF |
| 73 | PI | Butyl chloroformate | DMF |
| 74 | PI | Trichloroethylene | DMF |
| 75 | PI | 2,3-Dichloromaleic anhydride | DMF |

PI: Polyimide according to Example 2
PC: Bisphenol A polycarbonate (PC 3000 W)
Polyarylate: Polyester formed from terephthalic acid and Bisphenol A
DMF: Dimethylformamide
TCB: 1,2,4-Trichlorobenzene

EXAMPLES 76 and 77

100 mg of polyimide and 1.6 mg of tetraselenotetracene are dissolved in 10 g of dimethylformamide. 0.5 equivalent of the electron acceptors iron(III) chloride or nitronium tetrafluoroborate is then added to this solution. The solution is poured onto a heated sheet of glass and the solvent is allowed to evaporate under isothermal conditions at temperatures between 100° and 130° C. Conducting polymer films having an electrically conducting network of crystal needles are obtained; the conductivity, measured by the 4-point method, is 0.01–0.5 Scm$^{-1}$.

What is claimed is:

1. A compound of the formula II or IIa

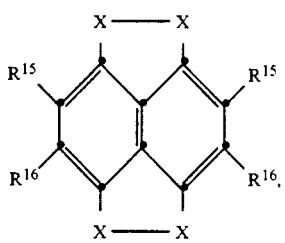
(II)

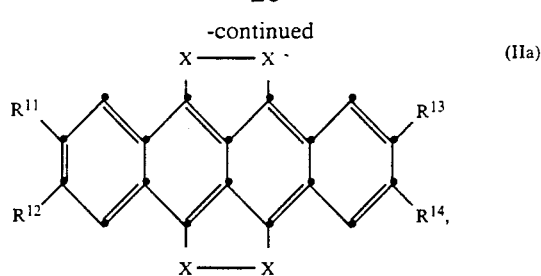
(IIa)

in which $R^{15}$ and $R^{16}$ are each phenylthio, 4-methylphenylthio, 4-methoxyphenylthio or 4-pyridylthio or in which $R^{15}$ and $R^{16}$ together are

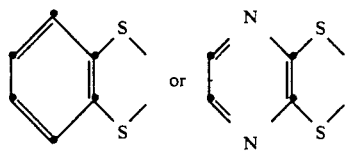

$R^{11}$, $R^{12}$, $R^{13}$ and $R^{14}$ are CH$_3$ or F, and X is S, Se or Te.

* * * * *